(12) United States Patent
Ikeda (10) Patent No.: US 10,264,378 B2
(45) Date of Patent: Apr. 16, 2019

(54) EAR MODEL, ARTIFICIAL HEAD, AND MEASUREMENT SYSTEM AND MEASUREMENT METHOD USING THE EAR MODEL AND ARTIFICIAL HEAD

(71) Applicant: Kyocera Corporation, Kyoto (JP)

(72) Inventor: Tomoyoshi Ikeda, Yokohama (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 15/030,814

(22) PCT Filed: Jun. 27, 2014

(86) PCT No.: PCT/JP2014/003448
§ 371 (c)(1),
(2) Date: Apr. 20, 2016

(87) PCT Pub. No.: WO2015/059847
PCT Pub. Date: Apr. 30, 2015

(65) Prior Publication Data
US 2016/0261964 A1    Sep. 8, 2016

(30) Foreign Application Priority Data
Oct. 23, 2013    (JP) .................................. 2013-220626

(51) Int. Cl.
*A61B 5/12* (2006.01)
*H04S 7/00* (2006.01)
(Continued)

(52) U.S. Cl.
CPC ............. *H04R 29/001* (2013.01); *A61B 5/12* (2013.01); *H04R 5/027* (2013.01); *H04R 29/00* (2013.01);
(Continued)

(58) Field of Classification Search
CPC ................................ H04R 29/00; H04R 25/30
(Continued)

(56) References Cited

U.S. PATENT DOCUMENTS 4,741,035 A    4/1988    Genuit
5,624,377 A    4/1997    Davis
(Continued)

FOREIGN PATENT DOCUMENTS

JP    S53-82301 A    7/1978
JP    S55-88497 A    7/1980
(Continued)

OTHER PUBLICATIONS

International Electrotechnical Commission, Electroacoustics—Simulators of human head and ear—Part 7: Head and torso simulator for the measurement of air-conduction hearing aids , 2nd Edition, Apr. 1, 2017 , pp. 1-38.*
(Continued)

*Primary Examiner* — Alexander Jamal
(74) *Attorney, Agent, or Firm* — Studebaker & Brackett PC (57) ABSTRACT

This measurement system is for evaluating an acoustic apparatus (100) that includes a vibrating element (102) and allows sound to be heard via vibration transmission. The measurement system includes an ear model (50) including an artificial ear (51) modeled after a human ear and an artificial temporal bone (57) in contact with the artificial ear (51); and a vibration detection element (56) disposed in the artificial temporal bone (57).

15 Claims, 5 Drawing Sheets

(51) Int. Cl.
  *H04R 29/00* (2006.01)
  *H04R 5/027* (2006.01)
  *H04R 25/00* (2006.01)
(52) U.S. Cl.
  CPC ............... *H04S 7/00* (2013.01); *H04R 25/30* (2013.01); *H04S 2420/01* (2013.01)
(58) Field of Classification Search
  USPC ............................................ 381/60, 58, 322
  See application file for complete search history.

(56) References Cited

U.S. PATENT DOCUMENTS

| | | | | |
|---|---|---|---|---|
| 6,402,782 | B1* | 6/2002 | Sibbald | H04R 29/00 623/10 |
| 7,616,767 | B2 | 11/2009 | Geiger et al. | |
| 2006/0126855 | A1 | 6/2006 | Geiger et al. | |
| 2006/0274901 | A1* | 12/2006 | Terai | H04S 1/005 381/17 |
| 2007/0009107 | A1* | 1/2007 | Lange | H04R 25/305 381/60 |
| 2009/0189313 | A1* | 7/2009 | Masters | H04R 25/608 264/328.1 |
| 2011/0182451 | A1* | 7/2011 | Vaarbroe | H04R 25/608 381/322 |
| 2015/0341733 | A1 | 11/2015 | Ikeda | |

FOREIGN PATENT DOCUMENTS

| | | |
|---|---|---|
| JP | S58-198338 A | 11/1983 |
| JP | H11-500284 A | 1/1999 |
| JP | 2002-315098 A | 10/2002 |
| JP | 2005-348193 A | 12/2005 |
| JP | 2006-157318 A | 6/2006 |
| JP | 2007-228508 A | 9/2007 |
| JP | 4237424 B2 | 3/2009 |
| JP | 2009-232443 A | 10/2009 |
| JP | 2013-143612 A | 7/2013 |
| WO | 93/11648 A1 | 6/1993 |
| WO | 2014/080557 A1 | 5/2014 |

OTHER PUBLICATIONS

International Search Report, PCT/JP2014/003448 dated Aug. 5, 2014.
Written Opinion of the International Searching Authority with Concise Explanation, PCT/JP2014/003448, dated Aug. 5, 2014.
An Office Action; "Notice of Reasons for Rejection," issued by the Japanese Patent Office dated Jul. 12, 2016, which corresponds to Japanese Patent Application No. 2015-104114 and is related to U.S. Appl. No. 15/030,814; with English language statement of relevance.
An Office Action issued by the Russian Patent Office dated Apr. 17, 2017, which corresponds to Russian Patent Application No. 2016115729 and is related to U.S. Appl. No. 15/030,814; with English language translation.
"Akustik—Simulatoren des menschlichen Kopfes und Ohres—Teil 7: Kopf—und Rumpfsimulator fur Messungen an Horgeraten (IEC/TS 60318-7:2011) / Electroacoustic—Simulators of human head and ear—Part 7: Head and torso simulator for the measurement of hearing aids (IEC/TS 60318-7:2011)"; DIN IEC/TS 60318-7 DIN SPEC 45608; Feb. 2012; pp. 1, 6, 8 and 11; with English translation.
An Office Action issued by the Chinese Patent Office dated Mar. 2, 2018, which corresponds to Chinese Patent Application No. 201480057142.X and is related to U.S. Appl. No. 15/030,814; with English language translation.
Clavier et al., "Measurements of bone-conducted impulse noise from weapons using a head simulator", Conference Paper in The Journal of the Acoustical Society of America, Oct. 2012, 2 pages.
Suzuki et al., "Rapid Prototyping of Temporal Bone for Surgical Training and Medical Education", Taylor & Francis healthsciences, Acta Otolaryngol 2004; 124: p. 400-402.
Chiao-Ling Liao, "Application of cross-talk cancellation to the improvement of binaural directional properties for individuals using bone anchored hearing aids (BAHA)", Master's Thesis in the Master's programme in Sound and Vibration, Chalmers University of Technology, 2010, 62 pages, Goteborg, Sweden.

* cited by examiner

EAR MODEL, ARTIFICIAL HEAD, AND MEASUREMENT SYSTEM AND MEASUREMENT METHOD USING THE EAR MODEL AND ARTIFICIAL HEAD

CROSS-REFERENCE TO RELATED APPLICATION

This application claims priority to and the benefit of Japanese Patent Application No. 2013-220626 filed Oct. 23, 2013, the entire contents of which are incorporated herein by reference.

TECHNICAL FIELD

This disclosure relates to a measurement system and the like for evaluating an acoustic apparatus, such as an earphone or headphone, that allows sound to be heard via vibration transmission by placing the acoustic apparatus, which includes a vibrating body, within a human ear or pressing the acoustic apparatus against the ear.

BACKGROUND

JP 2005-348193 A (PTL 1) recites an acoustic apparatus, such as a mobile phone or the like, that transmits air-conducted sound and bone-conducted sound to a user. As the air-conducted sound, PTL 1 discloses a sound that is transmitted to the user's auditory nerve by air vibrations, caused by a vibrating object, that are transmitted through the external ear canal to the eardrum and cause the eardrum to vibrate. As the bone-conducted sound, PTL 1 discloses a sound that is transmitted to the user's auditory nerve through a portion of the user's body (such as the cartilage of the outer ear) that is contacting a vibrating object.

In the telephone disclosed in PTL 1, a rectangular plate-shaped vibrating body, formed from a piezoelectric bimorph and a flexible substance, is attached to an outer surface of a housing via an elastic member. PTL 1 discloses that when voltage is applied to the piezoelectric bimorph in the vibrating body, the piezoelectric material expands and contracts in the longitudinal direction, causing the vibrating body to vibrate. Air-conducted sound and bone-conducted sound are transmitted to the user when the user contacts the vibrating body to the auricle.

Apart from a telephone or the like that transmits sound by being held in the hand and pressed against the ear, other devices that could transmit sound based on such a transmission principle include earphones and headphones that are used by being hooked and held somewhere on the human head.

CITATION LIST

Patent Literature

PTL 1: JP 2005-348193 A

SUMMARY (Technical Problem)

In order to evaluate an acoustic apparatus that is configured to transmit bone-conducted sound to the user via cartilage of the outer ear, such as the above-described telephone and the earphones or headphones used by being held somewhere on the human head including the ear, I recognized the necessity of measuring the amount of vibration that acts approximately on the human auditory nerve due to vibration of the vibrating body.

It would therefore be helpful to provide a measurement system, a measurement method, and various members and the like usable in the measurement system and measurement method, that can measure an amount of vibration weighted for the characteristics of vibration transmission in a human ear and that can evaluate an acoustic apparatus that includes a vibrating body.

(Solution to Problem)

My measurement system is for evaluating an acoustic apparatus that includes a vibrating element and allows sound to be heard via vibration transmission, and the measurement system includes an ear model including an artificial ear modeled after a human ear and an artificial temporal bone in contact with the artificial ear; and a vibration detector disposed in the artificial temporal bone.

(Advantageous Effect)

According to this disclosure, the amount of vibration that takes into account the characteristics of vibration transmission via a human ear and temporal bone can be measured, and a variety of acoustic apparatuses, hearing aids, or the like that include a vibrating body and vibrate the auricle can be evaluated.

DETAILED DESCRIPTION

The following describes embodiments with reference to the drawings.

Embodiment 1

Figure 1:
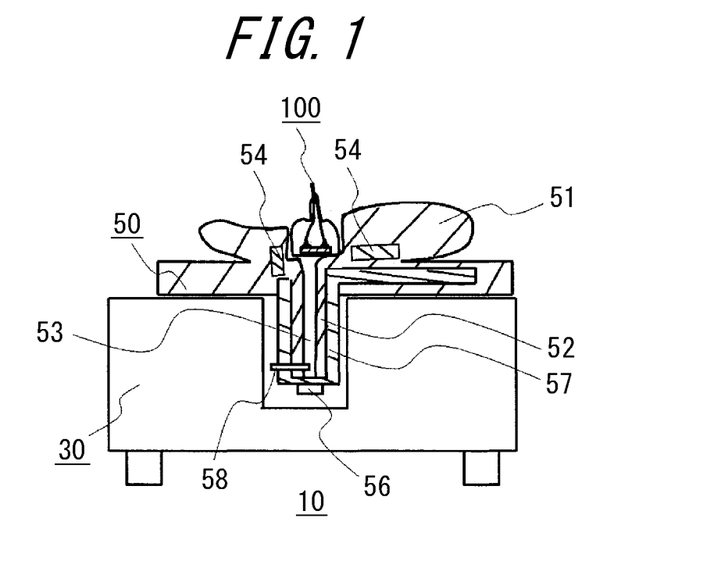
FIG. 1 is a cross-sectional view schematically illustrating the structure of a measurement system according to Embodiment 1.
Figure 2:
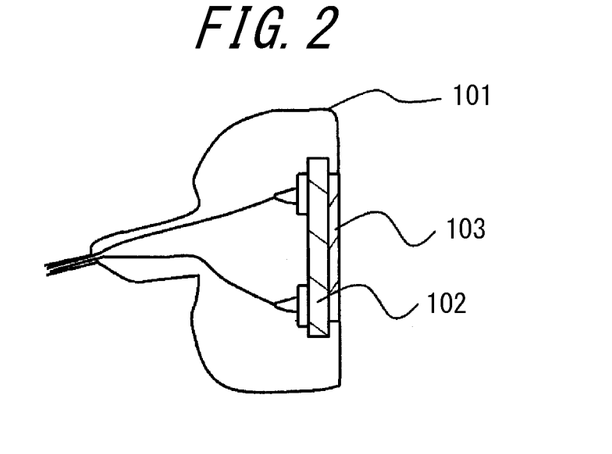
FIG. 2 is a cross-sectional view illustrating an earphone that is an example of a measurement target.

FIG. 1 schematically illustrates the structure of a measurement system according to Embodiment 1. A measurement system 10 according to this embodiment includes an ear model 50 supported on a base 30. The following describes a cartilage conduction type earphone as an example of an acoustic apparatus 100. As illustrated in FIG. 2, the acoustic apparatus 100 includes a housing 101 to be inserted in the hole of the human ear and a piezoelectric element 102 within the housing 101. The housing 101 is vibrated by the piezoelectric element 102. The acoustic apparatus 100 includes a protective film formed by a rubber material 103 at a portion that abuts a human ear. The rubber material 103 is for mitigating external friction, shocks, or the like and is not essential. Accordingly, the protective film is preferably to be an object in the form of a film so as not to inhibit vibration transmission. The protective film may instead be a plate-shaped covering member that covers the piezoelectric element 102 and is made of acrylic resin or the like.

Next, the ear model 50 according to the disclosed measurement system is described.

As illustrated in FIG. 1, the ear model 50 is supported by the base 30 around an artificial external ear canal unit 52. The ear model 50 may be detachable from the base 30. The ear model 50 may be secured with adhesive resin or double-sided tape.

The ear model 50 is modeled after a human ear and includes an artificial ear 51, an artificial external ear canal unit 52 joined to or formed integrally with the artificial ear 51, artificial cartilage 54 buried inside the artificial ear 51, and an artificial temporal bone 57 disposed so as to surround the artificial external ear canal unit 52.

The artificial ear 51 is a model of soft tissue of a human outer ear (excluding cartilage tissue). The artificial ear 51 is formed by an ear-shaped part and a part that has a size covering the ear-shaped part and that has a hole formed in the center. The hole is connected to a sound duct formed in the tubular artificial external ear canal unit 52, described below, and constitutes an artificial external ear canal 53.

Figure 4:
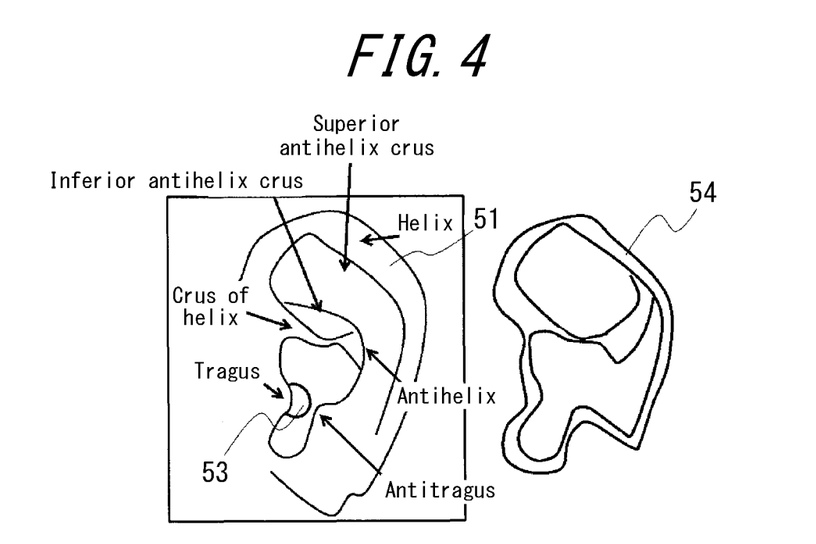
FIG. 4 is a plan view of an artificial ear and artificial cartilage.

The artificial ear 51 may, for example, be in approximately the same shape as the shape of an average artificial ear used in a manikin such as a Head And Torso Simulator (HATS) or KEMAR® (Knowles Electronics Manikin for Acoustic Research by Knowles Electronics (KEMAR is a registered trademark in Japan, other countries, or both)). The artificial ear 51 may, for example, be formed from a substance configured with material conforming to IEC60318-7. This material may, for example, be formed with silicone rubber or the like having a Shore hardness of 30 to 60 (such as a Shore hardness of 35 or 55). By providing the artificial cartilage 54 in this embodiment, the hardness after the artificial cartilage 54 is buried in the artificial ear 51 is, for example, set to be equivalent to the hardness of an existing ear model that does not include the artificial cartilage 54 and is made from material having a Shore hardness of 35 or 55. Therefore, the actual material of the artificial ear 51 may, for example, be a material with a Shore hardness of 35 or less, such as a material with a Shore hardness of 20 to 30. As illustrated in FIG. 4, a tragus, antitragus, helix, and the like may be formed in the artificial ear 51.

The artificial external ear canal unit 52 is connected to the hole provided in the artificial ear 51 and extends in a tubular shape in the opposite direction from the acoustic apparatus 100. The artificial external ear canal unit 52 for example has a Shore hardness of approximately 20 to 60 and is configured with the same substance as the artificial ear 51. The artificial external ear canal unit 52 may, for example, be a soft substance such as silicone rubber, natural rubber, or the like.

The artificial external ear canal unit 52 is difficult to process if the walls are too thin, whereas if the walls are too thick, it may be impossible to faithfully model the acoustic emission component of the external ear canal due to vibration transmission from the acoustic apparatus 100 (the component detected as air-conducted sound due to the inner wall of the external ear canal vibrating, which vibrates air in the external ear canal, thereby transmitting sound to the eardrum). Therefore, the artificial external ear canal unit 52 preferably has a thickness of, for example, approximately 0.3 mm to 2 mm and preferably has a diameter (inner diameter) of, for example, approximately 3 mm to 15 mm.

Figure 3:
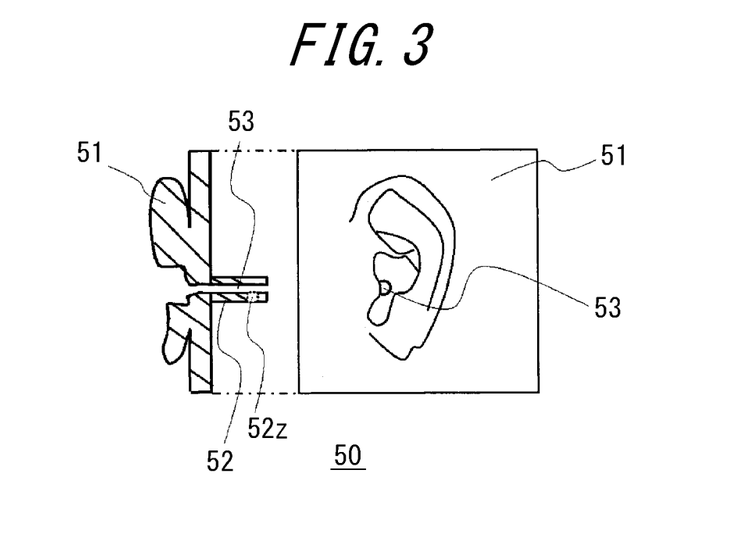
FIG. 3 is a cross-sectional view and a plan view of an artificial ear.

The artificial external ear canal unit 52 may of course be manufactured integrally with the artificial ear 51 by a mold, a 3D printer, or the like. The artificial external ear canal unit 52 and the artificial ear 51 may also be manufactured as separate members that are subsequently joined together with adhesive or the like. In this case, the adhesive preferably includes the same composition as the material of the artificial ear 51 and the artificial external ear canal unit 52. For example, when the artificial ear 51 and the artificial external ear canal unit 52 are silicone rubber, the adhesive is also preferably a silicone-based adhesive. In FIG. 3, the cross-section of the artificial external ear canal unit 52 has a rectangular, tubular shape, but the shape is not limited to being rectangular.

The length of the artificial external ear canal 53, i.e. the length from the opening of the hole provided in the artificial ear 51 to the end of the artificial external ear canal unit 52, preferably corresponds to the length from the opening in the hole of a human ear up to the eardrum (cochlea) and for example is appropriately set in a range of 10 mm to 40 mm. For example, the length of the artificial external ear canal 53 may be approximately 30 mm.

Furthermore, an insertion hole 52z for a probe microphone is provided at the end of the artificial external ear canal unit 52. Air-conducted sound and an emission component generated by the inner wall of the external ear canal vibrating air inside the external ear canal can be measured together by a microphone 58 inserted through the insertion hole 52z.

As illustrated in FIG. 4, the artificial cartilage 54 is buried inside the artificial ear 51. The artificial cartilage 54 models the cartilage of a human ear.

The artificial cartilage 54 maintains the shape of the artificial ear 51 and is suitable for more faithfully replicating transmission of vibration from the acoustic apparatus 100. The artificial cartilage 54 may, for example, be produced from a plastic such as polyethylene terephthalate (PET), natural rubber, or thinly molded polyvinyl chloride, or from a biomaterial such as lactic acid polymer, elastin, or the like. As described above, the material, thickness, and the like of the artificial cartilage 54 are adjusted so that the composite body resulting from burying the artificial cartilage 54 in the artificial ear 51 has flexural strength equivalent to that of an existing artificial ear formed from material with a Shore hardness of 35 or a Shore hardness of 55.

In order to support various types of acoustic apparatuses that are pressed against the ear in different ways, the artificial cartilage 54 is preferably located at sites corresponding to the tragus, antitragus, antihelix, inferior antihelix crus, superior antihelix crus, helix, and crus of helix, as illustrated in FIG. 4.

Among acoustic apparatuses, if measurement of only a certain type is envisioned, then it suffices to provide the artificial cartilage 54 only at essential sites corresponding to that type of acoustic apparatus. For example, the artificial cartilage 54 may be provided at only the tragus, or at only the tragus and the antitragus. The artificial cartilage 54 may use artificial cartilage that is obtained by cultivating cartilage cells, collected from an actual human body, a cow, a sheep, or the like, inside a lactic acid polymer mold, produced with a 3D printer, in the shape of cartilage.

Figure 5:
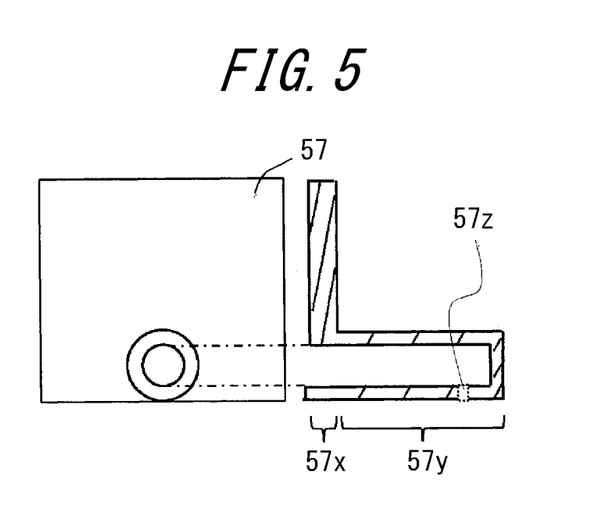
FIG. 5 is a cross-sectional view and a plan view of an artificial temporal bone.

As illustrated in FIG. 5, in broad terms the artificial temporal bone 57 is formed by a buried portion 57x that is buried inside the artificial ear 51 and a tubular portion 57y, for example in a cylindrical shape, that is connected to the buried portion 57x and surrounds the outside of the artificial external ear canal unit 52. The buried portion 57x and the tubular portion 57*y* may be formed integrally, or separately produced components may be connected.

The buried portion 57*x* may have a wide area similar to that of a temporal bone that includes the squamous part, external acoustic pore, petrous part, zygomatic process, and mastoid part of the temporal bone in the human body. For example, when only a bone conduction type earphone is targeted for measurement as the acoustic apparatus 100, the buried portion 57*x* may correspond simply to the external acoustic pore and its surroundings.

For example, one plate-shaped body is mainly used as the buried portion 57*x*. While a human temporal bone actually includes a mastoid part, a tympanic part with a complex shape, a zygomatic process, and the like, not all of these shapes are faithfully modeled. However, assuming the case of simultaneously contacting auricle cartilage and the zygomatic process (of course through the skin) when using a smartphone or the like that vibrates the entire touch panel and transmits air-conducted sound and sound based on the vibration, it has meaning to extend the artificial temporal bone 57 so as to provide broad coverage beyond the external acoustic pore and its surroundings, thereby allowing vibration components to be picked up over a wide area. Vibration generated in the artificial cartilage 54 buried in the artificial ear 51 is indirectly transmitted to the buried portion 57*x*. It is thus possible to simulate the vibration component that is transmitted from the soft tissue of the auricle to the auricle cartilage, passes through the temporal bone (external acoustic pore), and reaches the cochlea and the vibration component that is transmitted from soft tissue such as skin to the outer surface of the temporal bone (for example the mastoid part and the zygomatic process) through the external acoustic pore and reaches the inner ear.

Furthermore, the artificial temporal bone 57 includes the tubular portion 57*y*. The tubular portion 57*y* is a simplified model of a human external acoustic pore. The tubular portion 57*y* is a tubular member that surrounds the outer circumference of the artificial external ear canal unit 52, has a closed end, and contacts the buried portion 57*x* around a site corresponding to the external acoustic pore. Insofar as possible, the tubular portion 57*y* of the artificial temporal bone 57 is preferably joined to the artificial external ear canal unit 52, but assuming replacement due to wear of the artificial ear 51 over time, such joining is not essential. The tubular portion 57*y* preferably has a length and diameter that allow for housing inside the artificial external ear canal unit 52.

An insertion hole 57*z* for inserting a probe microphone 58 is provided at the end of the tubular portion 57*y*. The insertion hole 57*z* is in communication with the insertion hole 52*z* of the artificial external ear canal unit 52.

The artificial temporal bone 57 may, for example, be formed from a metal material such as SUS or aluminum, or from a hard resin material such as polycarbonate resin or acrylic resin. Furthermore, a porous layer may be provided on the main surface on one side of these materials. To form the porous layer, for example a porous plastic mold technique referred to as Microvent® (Microvent is a registered trademark in Japan, other countries, or both) by Taiseiplas Co., Ltd. may be used. The artificial temporal bone 57 may be caused to approach the temporal bone of a human body by, for example, integrally molding porous plastic onto the surface portion of a polycarbonate artificial temporal bone with a smooth surface.

Of course, the artificial temporal bone 57 may be configured with a material near that of a living organism, such as hydroxyapatite. By using such a material, the vibration characteristics can be considered near those of a human bone, and the degree of correction of the measurement values can be reduced.

The thickness differs by material, but for example in the case of the above-described metal material, the thickness may be approximately 0.1 mm to 1 mm, and in the case of hard resin material, the thickness may be approximately 2 mm to 5 mm. The artificial temporal bone 57 has an area sufficient to cover the entire ear portion of the artificial ear 51 and makes it easy to hold the artificial ear 51. The artificial temporal bone 57 is, for example, approximately 2.5 cm to 6 cm in both height and width. The artificial temporal bone 57 is partially joined to the above-described artificial ear 51 and artificial external ear canal unit 52. Therefore, vibration from the artificial external ear canal unit 52 or the artificial ear 51 propagates to the artificial temporal bone 57.

A vibration detector 55 is disposed in the ear model 50 outside the bottom of the tubular portion 57*y* of the artificial temporal bone 57. The vibration detector 55 includes a vibration detection element 56, such as a piezoelectric acceleration pickup. FIG. 1 illustrates the example of disposing the vibration detection element 56, which for example is chip-shaped, at the end of the tubular portion 57*y* of the artificial temporal bone 57. While it is possible to provide only one vibration detection element 56, a plurality of vibration detection elements 56 may also be disposed at appropriate intervals at the end of the tubular portion 57*y*. The lead wires for the vibration detection element 56, the probe microphone 58, and the like are omitted from the drawings. The vibration detection element 56 is attached to the artificial temporal bone 57 by adhesive or the like. Alternatively, the vibration detection element 56 may be secured by tape to the opposite side from a detection surface that contacts the bottom of the tubular portion.

The vibration detection element 56 disposed in the artificial temporal bone 57 can detect any or all of vibration that is conducted from the auricle cartilage through the temporal bone, vibration that is conducted from soft tissue of the cheek through the zygomatic bone, vibration that occurs when the vibrating portion of the acoustic apparatus is placed by the external acoustic pore and that is transmitted through a bone constituting the external acoustic pore, and the like.

The vibration detection element 56 may, for example, be selected from among commercially available elements, such as the ultra-compact and lightweight type NP-2106 by Ono Sokki Co. Ltd., or the PV-08A or PV-90B by Rion Co., Ltd. A vibration detection element 56 of approximately 0.2 g, such as the TYPE 7302 by Aco Co., Ltd., is a lightweight, appropriate vibration detection element.

The probe microphone 58 is provided at the end of the artificial external ear canal unit 52 (a position corresponding to a human eardrum). The microphone 58 detects air-conducted sound that has passed through the artificial external ear canal 53. The microphone 58 detects an air-conducted emission component generated at the sites of the artificial ear 51 or the inner walls of the artificial external ear canal unit 52 due to these sites vibrating.

The following describes a holder structure in which the acoustic apparatus 100, such as an earphone, is held. As illustrated in FIG. 1, when the acoustic apparatus 100 is a vibration transmission type earphone, the housing 101 of the earphone is partially or entirely inserted in the hole of the ear. The ear model 50 models the shape of a human ear and is provided with an auricle and external ear canal. Therefore, the earphone may be inserted into the auricle or external ear canal. In other words, the ear hole of the artificial ear 51 functions as a holding structure. In the case of a hearing aid that hooks onto the ear, the auricle itself of the artificial ear 51 functions as a holding structure.

Figure 6:
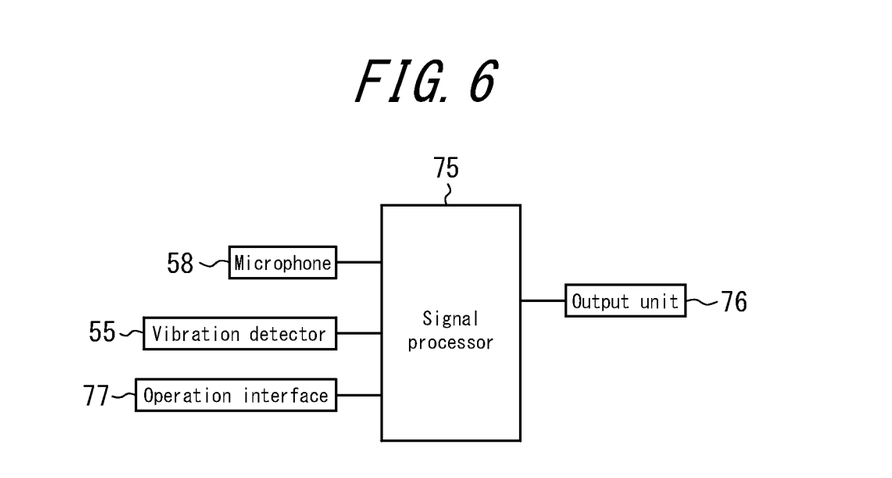
FIG. 6 is a functional block diagram of a section of the measurement system in FIG. 1.

FIG. 6 is a functional block diagram of a section of a measurement system 10 according to this embodiment. The vibration detector 55 provided with one or a plurality of vibration detection elements 56 is connected to a signal processor 75. Based on the output of each vibration detection element 56, the signal processor 75 calculates the amount of vibration propagating within the human body from the acoustic apparatus 100. Selection of the vibration detection element 56 for which input is to be detected and evaluated may be allowed with an operation interface 77 configured with a touch panel, push keys, or the like, or the amount of vibration of the vibration detection elements 56 may be averaged. The signal processor 75 processes the detection signal from the microphone 58. In this way, the sum of air-conducted sound from the acoustic apparatus 100 and air-conducted sound generated within the human body by vibration can be detected and evaluated.

The processing by the signal processor 75 may, for example, include generation of a measurement signal (pure tone, pure tone sweep, multi-sine wave, or the like). The signal processor 75 may include an equalizer and a dynamic range compressor. The signal processor 75 may also perform processing such as phase shifting or synthesis of the detected signals, a fast Fourier transform, or the like. The signal processor 75 may also be configured to analyze subharmonic distortion or harmonic distortion. The signal processor 75 may perform conversion to a variety of file formats in accordance with the output format of an output unit 76. The measurement results processed by the signal processor 75 are output to the output unit 76 such as a display, a printer, a memory, or the like and provided for evaluation of the acoustic apparatus 100.

In this way, the measurement system 10 according to this embodiment can measure the air-conducted sound level at a human eardrum and the vibration level weighted for characteristics of vibration transmission in a human ear, hence allowing accurate evaluation of the acoustic apparatus 100.

The correlation between the vibration level corresponding to vibration transmission through human cartilage and the sound pressure level corresponding to the detected value of vibration by the vibration detection element 56 can be obtained in advance when initially producing the measurement system by correction using an adjustment method or threshold method with multiple actual subjects, as is known. The vibration component is preferably corrected using people with conductive hearing loss as subjects.

Embodiment 2

Figure 7:
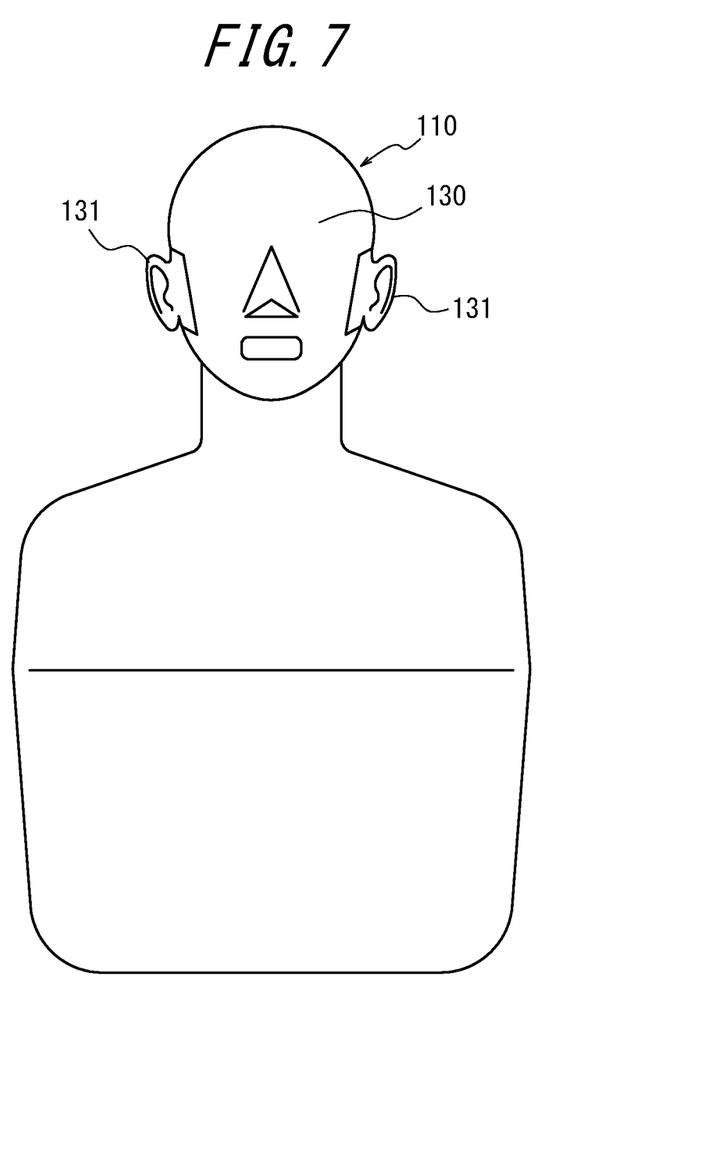
FIG. 7 schematically illustrates the structure of a measurement system according to Embodiment 2.

FIG. 7 schematically illustrates the structure of a measurement system according to Embodiment 2. A measurement system 110 according to this embodiment further includes a human head model 130. The ear model 50, measurement-related components, and signal processing may be the similar to those of the above-described embodiment. The head model 130 may, for example, be made of a material similar to HATS, KEMAR, or the like, but a relatively large cavity is provided inside the head to allow storage of the above-described ear model 50 and measurement-related components such as the microphone 58 or the vibration detector 55. The ear model 50 of the head model 130 is detachable from the head model 130. In other words, a portion or all of the ear model 50 may be an interchangeable part. For example, since the artificial ear 51 is made of resin, its vibration characteristics may change due to wear over time. Using interchangeable parts is effective for preventing such change in vibration characteristics.

The head model 130 is further provided with the parts of the skull other than the human temporal bone, and the above-described artificial temporal bone 57 is a portion of the skull. In other words, the head model 130 includes the zygomatic bone, maxilla, mandible, and the like, and the artificial temporal bone 57 may be joined to these parts.

The measurement system 110 of this embodiment yields measurement results that are at least similar to those of the measurement system 10 of Embodiment 1. Among other effects, in this embodiment, the acoustic apparatus 100 is evaluated by detachably mounting the ear model 50 on the human head model 130, thus allowing evaluation that conforms more closely to the actual form of use by taking into consideration the effect of vibration transmission in the head.

The present disclosure is not limited to the above embodiments, and a variety of modifications and changes are possible. For example, as the acoustic apparatus 100 targeted for measurement, the above embodiments focus on an acoustic apparatus, such as an earphone, in which a piezoelectric vibrator 102 vibrates and transmits vibration to the housing 101, so that the ear is vibrated via the housing. The acoustic apparatus is not, however, limited to this case. For example, the acoustic apparatus may be an apparatus that uses the touch panel in a smartphone as a vibrating plate, an apparatus that covers the entire ear such as a headphone held by a human head, an apparatus that transmits vibration to the ear via an acoustic apparatus provided in a head-mounted display, or an apparatus in which a vibrating element is embedded in the earpiece of a pair of eyeglasses and vibration of the earpiece transmits vibration sound.

Embodiment 3

Figure 8:
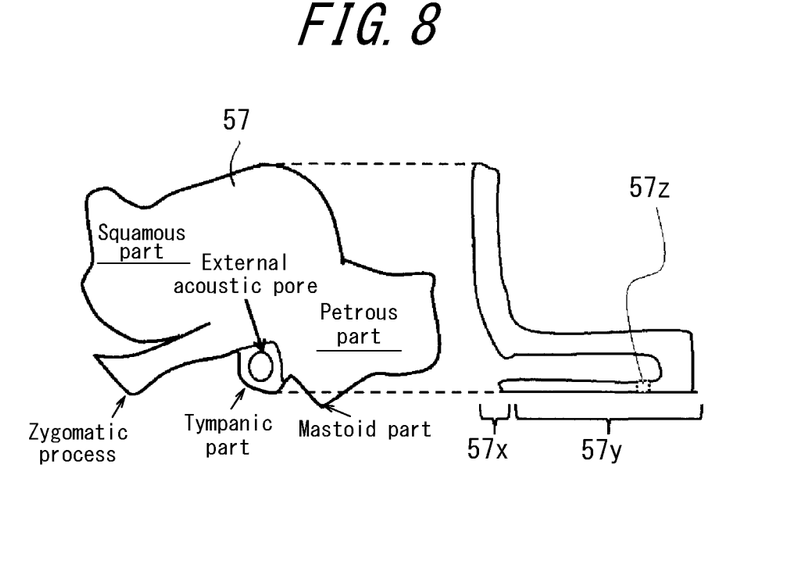
FIG. 8 is a cross-sectional view and a plan view of an artificial temporal bone according to Embodiment 3.

Next, a modification to the temporal bone 57 is illustrated in FIG. 8. According to this modification, apart from the external acoustic pore and squamous part, the temporal bone 57 includes the zygomatic process, tympanic part, mastoid part, petrous part, and the like. As a result, vibration occurring when the acoustic apparatus is placed or pressed against each site can be detected.

When made of resin, metal, or the like, the temporal bone 57 is preferably formed by casting in a mold. The temporal bone 57 may be produced with a plaster mold or the like. Forming the temporal bone 57 from calcium phosphate, such as hydroxyapatite that is a material suitable for living organisms, is optimal in terms of reproducing vibration characteristics.

Embodiment 4

Next, an example of a measurement method using the disclosed measurement system is described.

For example, a variety of measurements may be made by the following measurement steps. (1) A method for measuring an acoustic apparatus, the acoustic apparatus including a vibrating element and allowing sound to be heard via vibration transmission, the method including: placing the acoustic apparatus in contact with an ear model that includes an artificial ear modeled after a human ear and an artificial temporal bone in contact with the artificial ear; (2) causing the acoustic apparatus to generate a test sound; and (3) detecting vibration with a vibration detector disposed in the ear model.

The step of (4) detecting air-conducted sound with a microphone disposed in an artificial external ear canal of the ear model may be further included.

REFERENCE SIGNS LIST

10 Measurement system
30 Base
50 Ear model
51 Artificial ear
52 Artificial external ear canal unit
52z Insertion hole
53 Artificial external ear canal
54 Artificial cartilage
55 Vibration detector
56 Vibration detection element
57 Artificial temporal bone
57x Buried portion
57y Tubular portion
57z Insertion hole
58 Microphone
100 Acoustic apparatus
101 Housing
102 Vibrating element
103 Rubber material
110 Measurement system
130 Head model

The invention claimed is:

1. A measurement system for evaluating an acoustic apparatus, the acoustic apparatus causing a user to hear sound by vibration of a vibrating element, the measurement system comprising:
an ear model including an artificial ear modeled after a human ear and an artificial external ear canal unit continuous with the artificial ear, the artificial ear canal unit constituting an artificial external ear canal; and
a microphone configured to measure an air-conducted component inside the artificial external ear canal unit, wherein
with the acoustic apparatus in a state of contact with the artificial ear, vibration is transmitted from the artificial ear to the artificial external ear canal unit,
the artificial ear and the artificial external ear canal unit vibrate due to the vibration that is transmitted and generate an emission component that is a new air-conducted component, and
the microphone measures the air-conducted component inside the artificial external ear canal unit including the emission component,
the artificial ear and the artificial external ear canal unit are integrally formed or are formed by a same material,
the artificial external ear canal unit has a thickness in a range of 0.3 mm to 2.0 mm, and
a Shore hardness of the artificial external ear canal unit is from 20 to 60.

2. The measurement system of claim 1, wherein the microphone is disposed at an end of the artificial external ear canal unit.

3. The measurement system of claim 1, wherein the artificial ear and the artificial external ear canal unit continuous with the artificial ear are adhered to each another.

4. The measurement system of claim 1, wherein the microphone measures an air-conducted component generated by the acoustic apparatus together with the emission component generated in the artificial external ear canal unit.

5. The measurement system of claim 1, further comprising a tubular portion, wherein
the artificial external ear canal unit is joined to the tubular portion.

6. The measurement system of claim 1, further comprising a tubular portion, wherein
the artificial external ear canal unit is not joined to the tubular portion.

7. The measurement system of claim 1, wherein
the ear model further includes artificial cartilage buried in the artificial ear, and
the artificial cartilage is located at a position corresponding to a tragus in the artificial ear.

8. The measurement system of claim 1, further comprising a human head model, wherein
the ear model is attached to the head model.

9. The measurement system of claim 1, further comprising a base, wherein
the ear model is attached to the base.

10. The measurement system of claim 1, wherein the artificial ear includes a holding portion capable of holding the acoustic apparatus.

11. The measurement system of claim 8, wherein the head model includes a holding portion capable of holding the acoustic apparatus.

12. The measurement system of claim 1, wherein the ear model includes a portion formed from material conforming to IEC 60318-7.

13. A method for measuring an acoustic apparatus, the acoustic apparatus including a vibrating element and allowing sound to be heard via vibration transmission, the method including steps of:
holding the acoustic apparatus in contact with an ear model that includes an artificial ear modeled after a human ear and an artificial external ear canal unit in contact with the artificial ear the artificial ear canal unit constituting an artificial external ear canal;
causing the acoustic apparatus to generate a test sound; and
measuring, with a microphone disposed in the external ear canal of the ear model, an air-conducted component inside the artificial external ear canal unit including a newly generated emission component, the emission component being a new air-conducted component generated by the artificial ear and an inner wall of the artificial external ear canal unit vibrating due to vibration transmitted from the artificial ear to the artificial external ear canal unit with the acoustic apparatus in a state of contact with the artificial ear, wherein
the artificial ear and the artificial external ear canal unit are integrally formed or are formed by a same material,
the artificial external ear canal unit has a thickness in a range of 0.3 mm to 2.0 mm, and
a Shore hardness of the artificial external ear canal unit is from 20 to 60.

14. The measurement system according to claim 1, wherein
the artificial external ear canal unit has an inner diameter in a range of 3 mm to 15 mm.

15. The measurement system according to claim 13, wherein
the artificial external ear canal unit has an inner diameter in a range of 3 mm to 15 mm.

\* \* \* \* \*